US012788859B2

(12) United States Patent
Wagner et al.

(10) Patent No.: US 12,788,859 B2
(45) Date of Patent: Nov. 10, 2026

(54) PERITONEAL DIALYSIS SYSTEM HAVING AN AIR RETURN PATIENT LINE FILTER

(71) Applicants: BAXTER INTERNATIONAL INC., Deerfield, IL (US); BAXTER HEALTHCARE SA, Glattpark (CH)

(72) Inventors: Steffen Wagner, Deerfield, IL (US); Ralf Flieg, Deerfield, IL (US); Reinhold Buck, Deerfield, IL (US); Christof Beck, Deerfield, IL (US); Rainer Blickle, Deerfield, IL (US); Bernd Krause, Deerfield, IL (US); Torsten Knoer, Deerfield, IL (US)

(73) Assignees: VANTIVE US HEALTHCARE LLC, Deerfield, IL (US); VANTIVE HEALTH GMBH, Glattpark (CH)

( * ) Notice: Subject to any disclaimer, the term of this patent is extended or adjusted under 35 U.S.C. 154(b) by 272 days.

(21) Appl. No.: 18/710,246

(22) PCT Filed: Nov. 18, 2022

(86) PCT No.: PCT/US2022/080155
§ 371 (c)(1),
(2) Date: May 15, 2024

(87) PCT Pub. No.: WO2023/114611
PCT Pub. Date: Jun. 22, 2023

(65) Prior Publication Data

US 2025/0001059 A1 Jan. 2, 2025

Related U.S. Application Data

(60) Provisional application No. 63/291,036, filed on Dec. 17, 2021.

(51) Int. Cl.
*A61M 1/28* (2006.01)

(52) U.S. Cl.
CPC .................................. *A61M 1/287* (2013.01)

(58) Field of Classification Search
CPC .. A61M 1/287; A61M 1/1672; A61M 1/1658; A61M 1/285; A61M 1/28;
(Continued)

(56) References Cited

U.S. PATENT DOCUMENTS

| | | | |
|---|---|---|---|
| 6,758,971 B1 | 7/2004 | Haight | |
| 2007/0160495 A1 | 7/2007 | Schreyer | |

(Continued)

FOREIGN PATENT DOCUMENTS

| | | |
|---|---|---|
| CN | 1909938 A | 2/2007 |
| CN | 111132708 A | 5/2020 |

(Continued)

OTHER PUBLICATIONS

Brazilian Office Action, BR112024007411-0, mailed Feb. 18, 2026.

(Continued)

*Primary Examiner* — Dung T Ulsh
(74) *Attorney, Agent, or Firm* — K&L Gates LLP

(57) ABSTRACT

A peritoneal dialysis ("PD") system (10) includes a PD machine (20); a patient line (50) extending from the PD machine (20); a filter set (100) in fluid communication with the patient line (50), the filter set (100) including an air diverting net (112) configured to divert air from PD fluid flowing through the filter set (100); and an air return line (58) positioned to return PD fluid containing air back to the PD machine (20).

22 Claims, 4 Drawing Sheets

(58) Field of Classification Search
CPC .......... A61M 39/105; A61M 2205/126; A61M 2205/7536; B01D 61/243; B01D 63/02; B01D 63/06; B01D 63/08
See application file for complete search history.

(56) References Cited

U.S. PATENT DOCUMENTS

| | | | | |
|---|---|---|---|---|
| 2018/0021500 | A1* | 1/2018 | Gerber | A61L 2/022 604/29 |
| 2019/0083693 | A1 | 3/2019 | Biewer et al. | |
| 2020/0353144 | A1* | 11/2020 | Plahey | A61M 1/155 |

FOREIGN PATENT DOCUMENTS

| | | | |
|---|---|---|---|
| EP | 3 466 460 | A2 | 4/2019 |
| WO | 99/22783 | A1 | 5/1999 |

OTHER PUBLICATIONS

International Preliminary Report on Patentability from International Patent Application No. PCT/US2022/080155, issued Jun. 13, 2024. 9 pages.
International Search Report entered in PCT/US2022/080155.
Written Opinion entered in PCT/US2022/080155.
Chinese Office Action and English Translation for Chinese Patent Application No. 202280077791.0, dated Sep. 8, 2026. 17 pages.

* cited by examiner

PERITONEAL DIALYSIS SYSTEM HAVING AN AIR RETURN PATIENT LINE FILTER

CROSS-REFERENCE TO RELATED APPLICATION

The present application is a National Stage of International Application No. PCT/US2022/080155 filed on Nov. 18, 2022 which claims priority to and the benefit of U.S. Provisional Application No. 63/291,036, filed on Dec. 17, 2021, the entire contents of which are hereby incorporated by reference.

BACKGROUND

The present disclosure relates generally to medical fluid treatments and in particular to the filtering of treatment fluid during dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid or PD fluid, into a patient's peritoneal chamber via a catheter. The PD fluid comes into contact with the peritoneal membrane in the patient's peritoneal chamber. Waste, toxins and excess water pass from the patient's bloodstream, through the capillaries in the peritoneal membrane, and into the PD fluid due to diffusion and osmosis, i.e., an osmotic gradient occurs across the membrane. An osmotic agent in the PD fluid provides the osmotic gradient. Used PD fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used PD fluid to drain from the patient's peritoneal cavity. The patient then switches fluid communication so that the patient catheter communicates with a bag of fresh PD fluid to infuse the fresh PD fluid through the catheter and into the patient. The patient disconnects the catheter from the fresh PD fluid bag and allows the PD fluid to dwell within the patient's peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

APD is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh PD fluid and to a fluid drain. APD machines pump fresh PD fluid from a dialysis fluid source, through the catheter and into the patient's peritoneal chamber. APD machines also allow for the PD fluid to dwell within the chamber and for the transfer of waste, toxins and excess water to take place. The source may include multiple liters of dialysis fluid, including several solution bags.

APD machines pump used PD fluid from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

PD fluid needs to be sterile or very near sterile because it is injected into the patient's peritoneal cavity, and is accordingly considered a drug. While bagged PD fluid is typically properly sterilized for treatment, PD fluid made online or PD machines or cyclers that employ disinfection may need additional sterilization.

There is accordingly a need for an effective, low cost way of providing additional sterilization to fresh PD fluid before it is delivered to a patient.

SUMMARY

The present disclosure provides a peritoneal dialysis ("PD") system having a PD machine or cycler that pumps fresh PD fluid through a patient line to a patient and removes used PD fluid from the patient via the patient line. The patient line may be reusable or disposable and in either case operates with and fluidly communicates with a filter set. If the patient line is reusable, the reusable patient line is connected to the filter set at the time of treatment. If the patient line is disposable, the filter set is merged into the disposable patient line in one embodiment. In either configuration a distal end of the filter set may be connected to the patient's transfer set, which in turn communicates fluidly with the patient's indwelling catheter.

The PD machine or cycler may include a durable PD fluid pump that pumps PD fluid through the pump itself without using a disposable component, or a disposable type PD fluid pump including a pump actuator that actuates a disposable, fluid-contacting pumping component, such as a peristaltic pump tube or a flexible pumping chamber. It should be appreciated that while a single PD fluid pump may be used, dedicated fresh and used PD fluid pumps may be used alternatively. Also, a single PD fluid pump may include multiple pumping chambers for more continuous PD fluid flow. The PD machine or cycler also includes a plurality of valves, which may likewise be flow-through and durable without operating with a disposable component, or be disposable type valves having valve actuators that actuate a disposable, fluid-contacting valve component, such as a tube segment or a cassette-based valve seat.

The pumps and valves are under the automatic control of a control unit provided by the machine or cycler. In an embodiment, the valves include a fresh PD fluid valve that the control unit opens to allow the PD fluid pump to pump fresh PD fluid through a fresh PD fluid lumen of a dual lumen patient line to the patient. The valves also include a used PD fluid valve that the control unit opens to allow the PD fluid pump to pump used PD fluid from the patient through a used PD fluid lumen of the dual lumen patient line. The valves further include a supply valve that allows fresh PD fluid flow from one or more fresh PD fluid source, a drain valve that allows used PD fluid to be delivered to drain, and an air return valve that allows PD fluid containing air to be returned to the machine or cycler.

The fresh and used PD fluid lumens may again be reusable or disposable. In the instance in which the fresh and used PD fluid lumens are reusable, the lumens terminate with a connector that connects to a lumen-side connector of the filter set, which may be sealed to (e.g., ultrasonically sealed, heat sealed or solvent bonded) or molded with a body of the filter set. The body is in turn sealed to (e.g., ultrasonically sealed, heat sealed or solvent bonded) or molded with a transfer set-side connector that either connects directly to a mating connector of the patient's transfer set or to a mating connector of a short tube placed between the body and the patient's transfer set. The transfer set-side connector may alternatively simply be a port to which the short tube extends over for welding to the port.

The body of the filter set includes one or more filter membrane that further filters and sterilizes the fresh PD fluid so that it is suitable for delivery to a patient's peritoneal cavity. The one or more filter membrane may have any suitable shape, such as a tubular, capillary or flat shape. The filter membrane may be a sterilizing grade or bacteria reduction hydrophilic membrane, which may be formed with porous walls having a pore size of about 0.2 micron through which the fresh PD fluid flows for further filtration.

Used PD fluid removed through the patient's transfer set enters the body of the filter set via the transfer set-side connector and flows under negative pressure through the body, the lumen-side connector, and the used PD fluid lumen, back to the machine or cycler. The machine or cycler pumps the used PD fluid under positive pressure to drain. The used PD fluid may contact the outside of one or more filter membrane but may do so tangentially or in a tangential manner, wherein fibrin, proteins and other particulates within the patient's effluent do not tend to be trapped by or caught on the filter membranes. The filter membranes accordingly remain viable over the course of multiple fills of a treatment prior to being discarded with the filter set.

In one embodiment, the fresh and used PD fluid lumens are formed concentrically with the fresh PD fluid lumen located on the outside of the used PD fluid lumen. In an alternative embodiment, the fresh and used PD fluid lumens are formed in a side-by-side manner. A patient line connector may be provided at the ends of either the concentric or side-by-side lumens of the dual lumen patient line. The patient line connector connects to the lumen-side connector of the filter set. The lumen-side connector is in one embodiment provided with an air diverting net located along a fresh PD fluid inlet passageway so as to be upstream of the filter membranes. The air diverting net has mesh openings fine enough to divert air once wetted, but wherein the mesh openings are open enough not to significantly block the flow of fresh PD fluid.

The lumen-side connector includes multiple ports, e.g., tapered luer type ports, for sealing to mating ports of the patient line connector. The lumen-side connector ports include a fresh PD fluid port and a used PD fluid port. The fresh PD fluid port is provided with openings, such as slots that may be distributed evenly about the cylindrical fresh PD fluid port. The openings or slots allow a small amount of fresh PD fluid containing the air diverted by the air diverting net in the lumen-side connector to be pushed back to the PD machine or cycler via a third or air return line. The lumen-side connector may also include an outer port that in part defines a channel located between an inner wall of the outer port and an outer wall of the fresh PD fluid port. The channel directs the small amount of fresh PD fluid containing air into a sealed collection area within the patient line connector. The small amount of fresh PD fluid containing air exits the sealed area of the patient line connector to the machine or cycler, e.g., under negative pressure from the PD fluid pump, via an air return port and a flexible air return line. The air return port and flexible air return line may be small in diameter since the volume of returned PD fluid is small. The flexible air return line is reusable or disposable depending on whether the dual lumen patient line is reusable or disposable. The flexible air return line may be freestanding or be coextruded with the dual lumen patient line.

The flexible air return line connects to an internal and durable air return line located within the machine or cycler. The internal or durable air return line may extend to a location upstream or downstream from one or more supply valve. If the location is upstream of the one or more supply valve, then the one or more supply valve may also serve as the valve(s) opening and closing the air return PD fluid flow. If the location is downstream of the one or more supply valve, then the air return line may be provided with an air return valve that is selectively opened during a patient fill to allow air entrained PD fluid to be returned upstream of the PD fluid pump. The air return PD fluid flow may take place over an entire patient fill or intermittently during the patient fill.

The PD machine or cycler includes an airtrap located between the location at which the air return line reconnects with the primary PD fluid line and the PD fluid pump. The airtrap provides a volume of relatively stagnant PD fluid that allows air to escape from the fluid via buoyance. The airtrap accordingly helps to remove air that has been redirected to the PD machine or cycler via the air return features described herein.

In light of the disclosure set forth herein, and without limiting the disclosure in any way, in a first aspect of the present disclosure, which may be combined with any other aspect, or portion thereof, a peritoneal dialysis ("PD") system includes a PD machine; a patient line extending from the PD machine; a filter set in fluid communication with the patient line, the filter set including an air diverting net configured to divert air from PD fluid flowing through the filter set; and an air return line positioned to return PD fluid containing air back to the PD machine (20).

In a second aspect of the present disclosure, which may be combined with any other aspect, or portion thereof, the air diverting net is further configured to allow fresh PD fluid to pass through the air diverting net.

In a third aspect of the present disclosure, which may be combined with any other aspect, or portion thereof, the filter set further includes at least one filter membrane configured to filter the PD fluid that has passed through the air diverting net.

In a fourth aspect of the present disclosure, which may be combined with any other aspect, or portion thereof, the filter set is configured such that used PD fluid flows tangentially along the at least one filter membrane.

In a fifth aspect of the present disclosure, which may be combined with any other aspect, or portion thereof, the PD machine includes a PD fluid pump, and wherein the air return line extends to an air return line of the PD machine, the PD machine air return line extending to an inlet of the PD fluid pump.

In a sixth aspect of the present disclosure, which may be combined with any other aspect, or portion thereof, the PD machine includes an airtrap, and wherein the air return line extends to an air return line of the PD machine, the PD machine air return line in fluid communication with the airtrap.

In a seventh aspect of the present disclosure, which may be combined with any other aspect, or portion thereof, the air return line is coextruded with the patient line.

In an eighth aspect of the present disclosure, which may be combined with any other aspect, or portion thereof, the patient line includes a patient line connector for connecting to a lumen-side connector of the filter set, and wherein the air return line extends from the patient line connector to the PD machine.

In a ninth aspect of the present disclosure, which may be combined with any other aspect, or portion thereof, the lumen-side connector includes a fresh PD fluid port for receiving fresh PD fluid from the patient line, the fresh PD fluid port including at least one opening for allowing air diverted by the air diverting net to be returned to the PD machine via the air return line.

In a tenth aspect of the present disclosure, which may be combined with any other aspect, or portion thereof, the at least one opening is in fluid communication with a channel formed by the lumen-side connector, the channel extending so as to direct air diverted by the air diverting net towards an air return port of the patient line connector.

In an eleventh aspect of the present disclosure, which may be combined with any other aspect, or portion thereof, the patient line connects to a lumen-side connector of the filter set, and wherein the air return line extends from the lumen-side connector to the PD machine.

In a twelfth aspect of the present disclosure, which may be combined with any other aspect, or portion thereof, the patient line is a dual lumen patient line including a fresh PD fluid lumen and a used PD fluid lumen, and wherein the air return line is a third line extending between the filter set and the PD machine.

In a thirteenth aspect of the present disclosure, which may be combined with any other aspect, or portion thereof, the PD system includes a patient line connector for connecting to a lumen-side connector of the filter set, and wherein the fresh and used PD fluid lumens are connected to the patient line connector.

In a fourteenth aspect of the present disclosure, which may be combined with any other aspect, or portion thereof, the filter set includes a lumen-side connector, and wherein the fresh and used PD fluid lumens are connected to the lumen-side connector.

In a fifteenth aspect of the present disclosure, which may be combined with any other aspect, or portion thereof, the filter set is configured to connect directly to a patient's transfer set, or wherein the filter set includes a flexible tube configured to connect to the patient's transfer set.

In a sixteenth aspect of the present disclosure, which may be combined with any other aspect, or portion thereof, the filter membrane is a sterilizing grade filter membrane or a bacteria reduction filter membrane.

In a seventeenth aspect of the present disclosure, which may be combined with any other aspect, or portion thereof, a filter set includes a body holding at least one filter membrane positioned and arranged such that fresh PD fluid flows through at least one porous wall of the at least one filter membrane prior to exiting the body; an air diverting net configured to divert air from the fresh PD fluid prior to reaching the at least one filter membrane; and a fresh PD fluid port for receiving the fresh PD fluid, the fresh PD fluid port including at least one opening for allowing air diverted by the air diverting net to be returned to a PD machine.

In an eighteenth aspect of the present disclosure, which may be combined with any other aspect, or portion thereof, the filter set includes a channel in fluid communication with the at least one opening, the channel extending so as to direct air diverted by the air diverting net for return to the PD machine.

In a nineteenth aspect of the present disclosure, which may be combined with any other aspect, or portion thereof, the filter set includes a connector for connecting to a patient line connector, the air diverting net provided by the connector.

In a twentieth aspect of the present disclosure, which may be combined with any other aspect, or portion thereof, the filter set includes a connector for connecting to a patient line connector, the fresh PD fluid port provided by the connector.

In a twenty-first aspect of the present disclosure, which may be combined with any other aspect, or portion thereof, the at least one filter membrane has a tubular, capillary or flat shape.

In a twenty-second aspect of the present disclosure, which may be combined with any other aspect, or portion thereof, the filter set includes (i) a transfer set-side connector configured to connect to a patient's transfer set, or (ii) a flexible line configured to connect to the patient's transfer set.

In a twenty-third aspect of the present disclosure, which may be combined with any other aspect, or portion thereof, any of the features, functionality and alternatives described in connection with any one or more of FIGS. 1 to 4 may be combined with any of the features, functionality and alternatives described in connection with any other of FIGS. 1 to 4.

It light of the above aspects and description herein, is an advantage of the present disclosure to provide a filter set that operates with a dual lumen patient line.

It is another advantage of the present disclosure to provide a filter set that filters fresh PD fluid and allows used PD fluid to pass without clogging.

It is a further advantage of the present disclosure to provide a filter set that removes air before reaching the filter membranes.

It is yet another advantage of the present disclosure to provide a filter set that removes air without requiring a hydrophobic membrane.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
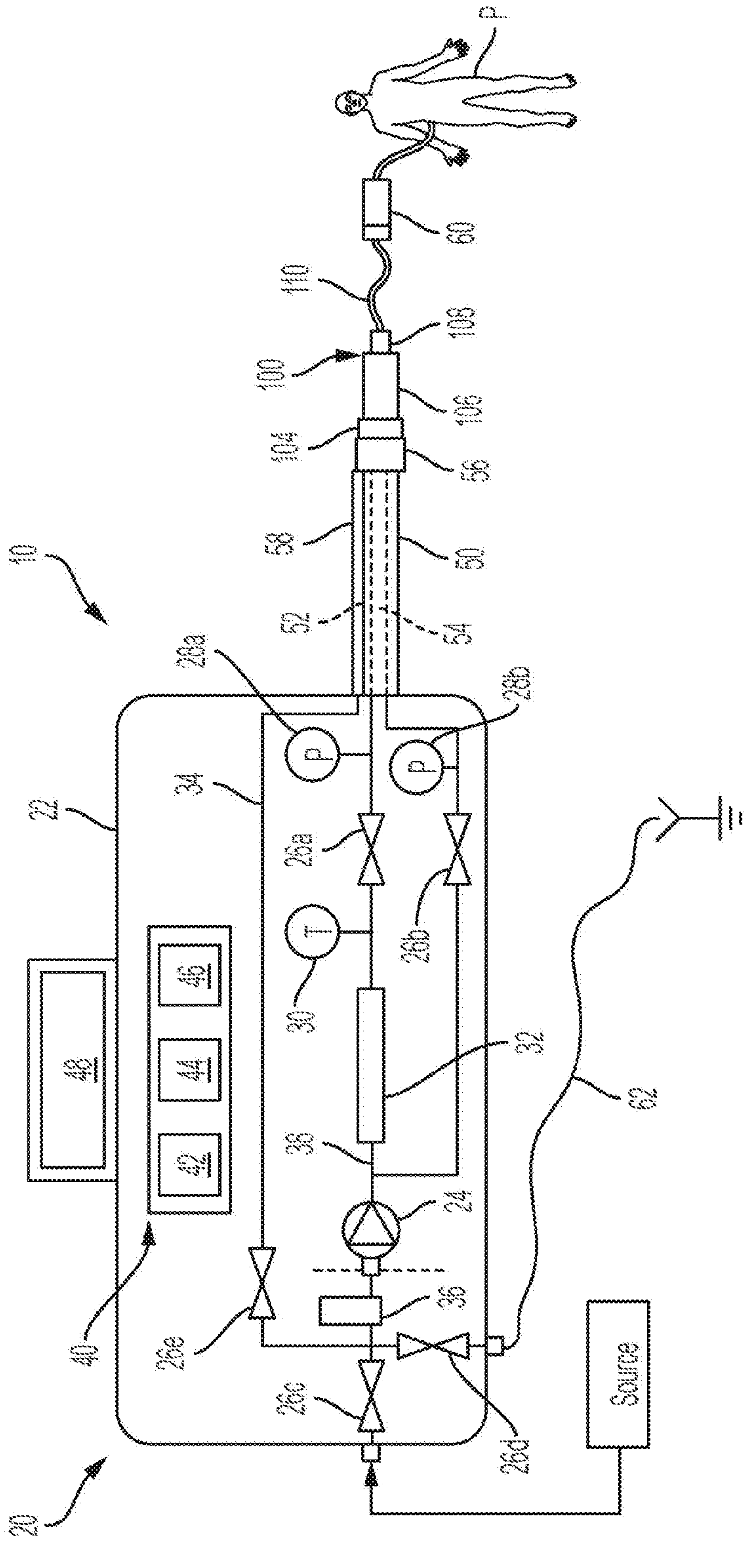
FIG. 1 is a schematic view of one embodiment for peritoneal dialysis system having a patient line filter set of the present disclosure.

Referring now to the drawings and in particular to FIG. 1, a peritoneal dialysis ("PD") system 10 is illustrated. PD system 10 includes a PD machine or cycler 20 that pumps fresh PD fluid through a patient line 50 to a patient P and removes used PD fluid from patient P via patient line 50. Patient line 50 may be reusable or disposable and in either case operates with and fluidly communicates with a filter set 100. If patient line 50 is reusable, the reusable patient line is connected to filter set 100 at the time of treatment. If patient line 50 is instead disposable, filter set 100 is merged into or formed with disposable patient line 50 in one embodiment. In either configuration, a distal end of filter set 100 may be connected to the patient's transfer set 60, which in turn communicates fluidly with the indwelling catheter of patient P.

PD machine or cycler 20 may include a housing 22 providing a durable PD fluid pump 24 that pumps PD fluid through the pump itself without using a disposable component. Examples of durable pumps that may be used for PD fluid pump 24 include piston pumps, gear pumps and centrifugal pumps. Certain durable pumps, such as piston pumps are inherently accurate, so that machine or cycler 20 does not require additional volumetric control components. Other durable pumps, such as gear pumps and centrifugal pumps may not be as accurate, such that machine or cycler 20 provides a volumetric control device such as one or more flowmeter (not illustrated).

Pump 24 may alternatively be a disposable type PD fluid pump, which includes a pump actuator that actuates a disposable, fluid-contacting pumping component, such as a peristaltic pump tube or a flexible pumping chamber. Examples of disposable PD fluid pumps that may be used for PD fluid pump 24 include rotary or linear peristaltic pump actuators that actuate tubing, pneumatic pump actuators that actuate cassette sheeting, electromechanical pump actuators that actuate cassette sheeting and platen pump actuators that actuate tubing. It should be appreciated that while a single PD fluid pump 24 may be used, dedicated fresh and used PD fluid pumps may be used alternatively. Also, single PD fluid pump 24 may include multiple pumping chambers for more continuous PD fluid flow.

PD machine or cycler 20 also includes a plurality of valves 26*a* to 26*e*, which may likewise be flow-through and durable without operating with a disposable component, or be disposable type valves having valve actuators that actuate a disposable, fluid-contacting valve component, such as a tube segment or a cassette-based valve seat. Examples of durable valves that may be used for valves 26*a* to 26*e* include flow-through solenoid valves. Such valves may be two-way or three-way valves. Examples of disposable valves that may be used for valves 26*a* to 26*e* include solenoid pinch valves that pinch closed flexible tubing, pneumatic valve actuators that actuate cassette sheeting, and electromechanical valve actuators that actuate cassette sheeting.

Machine or cycler 20 likely includes many valves 26*a* to 26*n*. For ease of illustration, machine or cycler 20 is shown having a fresh PD fluid valve 26*a* that is controlled to open to allow PD fluid pump 24 to pump fresh PD fluid under positive pressure through a fresh PD fluid lumen 52 of dual lumen patient line 50 to patient P. The valves also include a used PD fluid valve 26*b* that is controlled to open to allow PD fluid pump 24 to pull used PD fluid from patient P under negative pressure through a used PD fluid lumen 54 of dual lumen patient line 50. One or more supply valve 26*c* is provided, which allows fresh PD fluid flow from one or more fresh PD fluid source to be pumped into cycler 20 via PD fluid pump 24. A drain valve 26*d* is provided, which allows used PD fluid to be delivered to drain. An air return valve 26*e* discussed in more detail below allows PD fluid containing air diverted within filter set 100 to be returned to PD machine or cycler 20.

Machine or cycler 20 in the illustrated embodiment also includes pressure sensors, such as pressure sensors 28*a*, 28*b*. Pressure sensor 28*a* is located just downstream from fresh PD fluid valve 26*a*, while pressure sensor 28*b* is located just upstream from used PD fluid valve 26. Pressure sensor 28*a* may accordingly sense the pressure in fresh PD fluid lumen 52 of dual lumen patient line 50 even if fresh PD fluid valve 26*a* is closed, while pressure sensor 28*b* may sense the pressure in used PD fluid lumen 54 of dual lumen patient line 50 even if used PD fluid valve 26*b* is closed. Additionally, pressure sensor 28*a* is positioned to sense the pressure of fresh PD fluid upstream from the filter membranes discussed herein during a patient fill. Pressure sensor 28*b* perhaps more importantly is positioned to sense the pressure of fresh PD fluid downstream from the filter membranes discussed herein during a patient fill.

Pump 24 and valves 26*a* to 26*e* in the illustrated embodiment are under the automatic control of control unit 40 provided by machine or cycler 20 of system 10, while pressure sensors 28*a*, 28*b* (and other sensors) output to control unit 40. Control unit 40 in the illustrated embodiment includes one or more processor 42, one or more memory 44 and a video controller 46. Control unit 40 receives, stores and processes signals or outputs from pressure sensors 28*a*, 28*b*, and other sensors provided by machine or cycler 20, such as one or more temperature sensor 30 and one or more conductivity sensor (not illustrated). Control unit 40 may use pressure feedback from one or more of pressure sensor 28*a*, 28*b* to control PD fluid pump 24 to pump dialysis fluid at a desired pressure or within a safe pressure limit (e.g., within 0.21 bar (three psig) of positive pressure to a patient's peritoneal cavity and −0.10 bar (−1.5 psig) of negative pressure from the patient's peritoneal cavity).

Control unit 40 uses temperature feedback from one or more temperature sensor 30 for example to control a heater 32, such as an inline heater to heat fresh PD fluid to a desired temperature, e.g., body temperature or 37° C. In one embodiment, heater 32 is used additionally to heat a disinfection fluid, such as fresh PD fluid, to disinfect PD fluid pump 24, valves 26*a* to 26*n*, heater 32 and all reusable fluid lines within machine or cycler 20 to ready the machine or cycler for a next treatment. The additional filtration discussed herein provides a layer of protection in addition to the heated fluid disinfection to ensure that the PD fluid is safe for delivery to patient P.

Video controller 46 of control unit 40 interfaces with a user interface 48 of machine or cycler 20, which may include a display screen operating with a touchscreen and/or one or more electromechanical button, such as a membrane switch. User interface 48 may also include one or more speaker for outputting alarms, alerts and/or voice guidance commands. User interface 48 may be provided with the machine or cycler 20 as illustrated in FIG. 1 and/or be a remote user interface operating with control unit 40. Control unit 40 may also include a transceiver (not illustrated) and a wired or wireless connection to a network, e.g., the internet, for sending treatment data to and receiving prescription instructions from a doctor's or clinician's server interfacing with a doctor's or clinician's computer.

Figure 2:
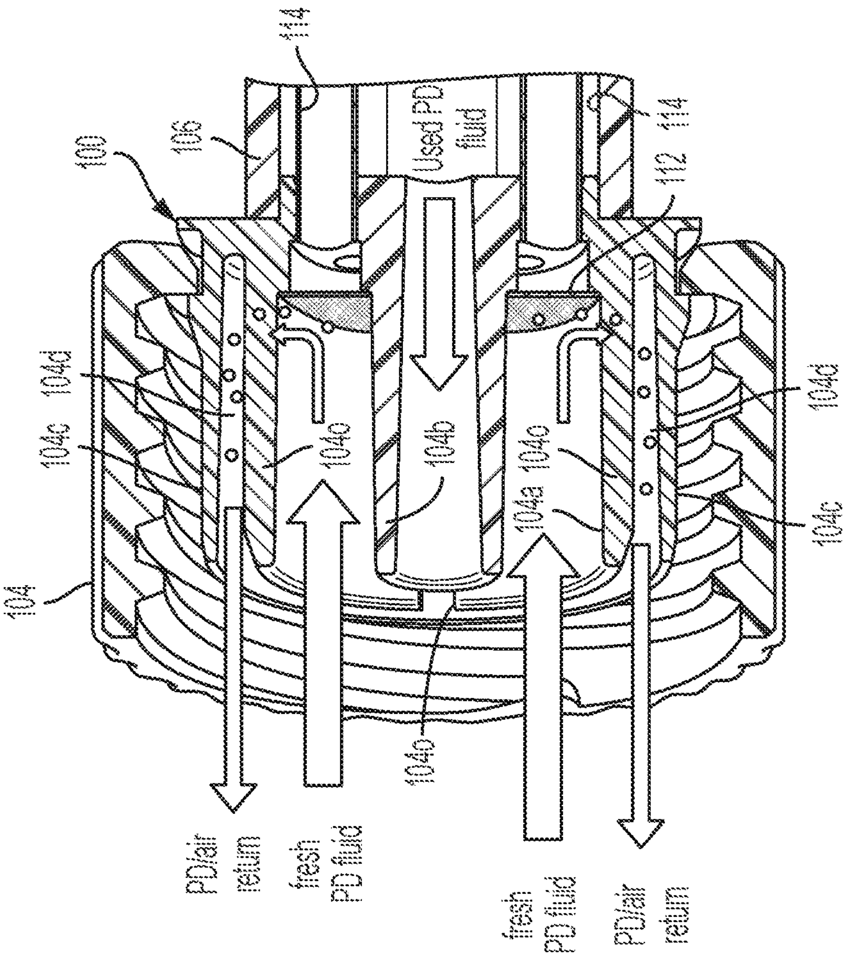
FIG. 2 is a sectioned perspective view of one embodiment for a lumen-side connector of the patient line filter set of the present disclosure.

Referring to FIGS. 1 and 2, as mentioned above, fresh and used PD fluid lumens 52 and 54 of dual lumen patient line 50 may again be reusable or disposable. In the instance in which dual lumen patient line 50 is reusable, the lumens terminate with a connector 56 that connects to a lumen-side connector 104 of filter set 100, which may be sealed to (e.g., ultrasonically sealed, heat sealed or solvent bonded) or molded with a body 106 of the filter set. A third or air return line 58, discussed in more detail below, delivers PD fluid containing air back from filter set 100 to PD machine or cycler 20. Body 106 is in turn sealed to (e.g., ultrasonically sealed, heat sealed or solvent bonded) or molded with a transfer set-side connector 108 that either connects directly to a mating connector of the patient's transfer set 60 or to a mating connector of a short, flexible tube 110 placed between transfer set-side connector 108 and the patient's transfer set 60. Body 106, lumen-side connector 104 and transfer set-side connector 108 may be made of any one or more plastic, such as, polystyrene ("PS"), polycarbonate ("PC"), blends of polycarbonate and acrylonitrile-butadiene-styrene ("PC/ABS"), polyvinyl chloride ("PVC"), polyethylene ("PE"), polypropylene ("PP"), polyesters like polyethylene terephthalate ("PET"), or polyurethane ("PU").

FIG. 2 illustrates one embodiment for lumen-side connector 104 in detail. The illustrated version of lumen-side connector 104 is for a concentric lumen 52 and 54 relationship for dual lumen patient line 50. It should be appreciated however that the teachings in connection with FIG. 2 are equally applicable to a side-by-side lumen 52 and 54 relationship for dual lumen patient line 50. Lumen-side connector 104 is in both the concentric and side-by-side embodiments provided with an air diverting net 112 located along a fresh PD fluid inlet passageway so as to be upstream (from a fresh PD fluid standpoint) of filter membranes 114. Air diverting net 112 has mesh openings fine enough to divert air once wetted, but wherein the mesh openings are open enough not to significantly block the flow of fresh PD fluid. Air diverting net 112 may for example be made of a medically safe metal or a hydrophobic polymer and may have a pore size in the range of from about 0.1 mm to about 0.3 mm. Air diverting net 112 may be sealed to lumen-side connector 104 ultrasonically, via heat and/or adhesively. Filter membranes 114 may be sterilizing grade or bacteria reduction hydrophilic membranes, which may formed with a porous wall having a pore size of about 0.2 micron through which fresh PD fluid flows for further filtration. Filter membranes 114 may be made from, for example, polysulfone or polyethersulfone blended with polyvinylpyrrolidone. Filter membranes 114 in the illustrated embodiment have a capillary shape but may alternatively have a tubular or flat shape.

The lumen-side connector 104 illustrated in FIG. 2 includes multiple ports, e.g., tapered luer type ports, for sealing to mating ports of patient line connector 56. The lumen-side connector ports include a fresh PD fluid port 104*a* and a used PD fluid port 104*b*, which may each be cylindrical ports that are concentric with each other. Used PD fluid removed through the patient's transfer set 60 enters body 106 of the filter set via transfer set-side connector 108 and flows under negative pressure through body 106, used PD fluid port 104*b* of lumen-side connector as illustrated in FIG. 2, and used PD fluid lumen 54, back to PD machine or cycler 20. PD machine or cycler 20 pumps the used PD fluid under positive pressure to drain via drain line 62. The used PD fluid may contact the outside of the one or more filter membrane(s) 114 but may do so tangentially or in a tangential manner, wherein fibrin, proteins and other particulates within the patient's effluent do not tend to be trapped by or caught on the filter membranes. Filter membranes 114 accordingly remain viable over the course of multiple fills of a treatment prior to being discarded with filter set 100.

Fresh PD fluid port 104*a* is provided with openings 104*o*, such as slots that may be distributed evenly, e.g., radially evenly, about the cylindrical fresh PD fluid port. In the illustrated example there are four slots 104*o* spaced evenly at 90° from each other. Openings 104*o* may alternatively be a series of holes, an array of holes, oblong shapes, for example. Openings or slots 104*o* allow a small amount of fresh PD fluid containing the air (shown as bubbles in FIG. 2) diverted by air diverting net 112 in lumen-side connector 104 to be pushed back to the PD machine or cycler 20 via a third or air return line 58.

Lumen-side connector 104 in the illustrated embodiment also includes an outer cylindrical port 104*c* that in part defines a cylindrical channel 104*d* located between an inner wall of cylindrical outer port 104*c* and an outer wall of cylindrical fresh PD fluid port 104*a*. Ports 104*a* to 104*c* are each molded with the remainder of lumen-side connector 104 in one embodiment.

Figure 3:
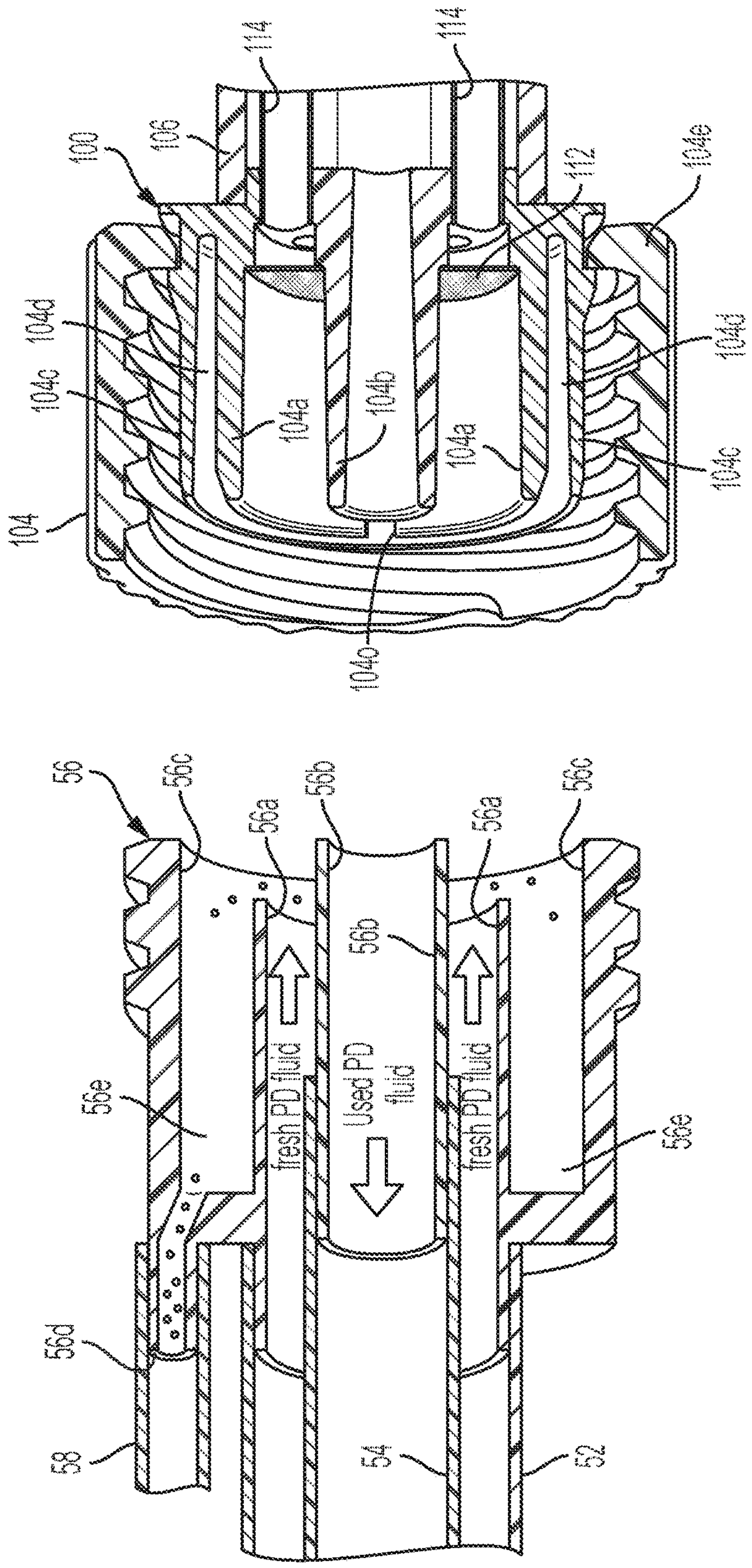
FIG. 3 is a sectioned view of the lumen-side connector of FIG. 2 and a mating patient line connector of the present disclosure.

FIG. 3 illustrates one possible mating arrangement between lumen-side connector 104 and patient line connector 56, which may likewise be molded and made of any of the materials discussed herein. The mating arrangement of FIG. 3 is specific to a concentric relationship between lumens 52 and 54. The mating arrangement between lumen-side connector 104 and patient line connector 56 would be different for a side-by-side relationship for lumens 52 and 54 but would still include the third or air return line 58 as discussed herein. In the illustrated embodiment, patient line connector 56 includes a cylindrical fresh PD fluid port 56*a* sized radially so that its outer surface seals against an inner surface of cylindrical fresh PD fluid port 104*a*, e.g., via a gasket such as silicone or other suitable rubber. The length of fresh PD fluid port 56*a* is sized to be short enough to allow at least a portion of openings or slots 104*o* of fresh PD fluid port 104*a* to be exposed to the flowing fresh PD fluid so that air is carried out through the exposed portions of the openings or slots 104*o*.

Patient line connector 56 also includes a cylindrical used PD fluid port 56*b* sized radially so that its inner surface seals against an outer surface of cylindrical used PD fluid port 104*b*, e.g., via a gasket such as silicone or other suitable rubber. Patient line connector 56 further includes a cylindrical outer wall 56*c* sized radially so that its inner surface seals against an outer surface of cylindrical outer cylindrical port 104*c*, e.g., via a gasket such as silicone or other suitable rubber. Cylindrical outer wall 56*c* in the illustrated embodiment includes outer facing threads that are configured to matingly and releasably thread to inner facing threads of an outer wall 104*e* of lumen-side connector 104. The threading of lumen-side connector 104 to patient line connector 56 makes each of the three seals discussed above in one embodiment.

FIG. 3 illustrates fresh PD fluid lumen 52 of dual lumen patient line 50 sealed, e.g., ultrasonically, heat and/or adhesively sealed, to fresh PD fluid port 56*a* of patient line connector 56. Used PD fluid lumen 54 is sealed in any desired manner to used PD fluid port 56*b*. Third or air return line 58 is sealed in any desired manner to an air return port 56*d* of patient line connector 56. When lumen-side connector 104 is mated to patient line connector 56 during a patient fill, channel 104*d* directs the small amount of fresh PD fluid containing air into a sealed collection area 56*e* located within patient line connector 56. The small amount of fresh PD fluid containing air exits sealed area 56*e* to PD machine or cycler 20, e.g., under negative pressure from PD fluid pump 24, via air return port 56*d* and flexible air return line 58. Air return port 56*d* and flexible air return line 58 may be small in diameter since the amount of returned PD fluid is small. Flexible air return line 58 is reusable or disposable depending on whether dual lumen patient line 50 is reusable or disposable. Flexible air return line 58 may be freestanding or be coextruded with dual lumen patient line 50.

FIG. 1 illustrates that flexible air return line 58 connects to an internal and durable air return line 34 located within PD machine or cycler 20. Internal or durable air return line 34 may extend to a location upstream of downstream from one or more supply valve 26*c*. If the location is upstream of one or more supply valve 26*c*, then the one or more supply valve may also serve as the valve(s) opening and closing the air return PD fluid flow via lines 58 and 34. If the location is downstream of one or more supply valve 26*c*, then cycler air return line 34 may be provided with an air return valve 26*e* that is selectively opened during a patient fill to allow air entrained PD fluid to be returned upstream of PD fluid pump 24. The air return PD fluid flow through lines 58 and 34 may take place over an entire patient fill or occur intermittently via the opening and closing of valve 26*e* during the patient fill.

PD machine or cycler 20 includes an airtrap 36 located between the location at which air return line reconnects with primary PD fluid line 38 and PD fluid pump 24. Airtrap 36 provides a volume of relatively stagnant PD fluid that allows air to escape from the fluid via buoyance. Airtrap 36 accordingly helps to remove air that has been redirected to PD machine or cycler 20 via the air return features described herein.

Figure 4:
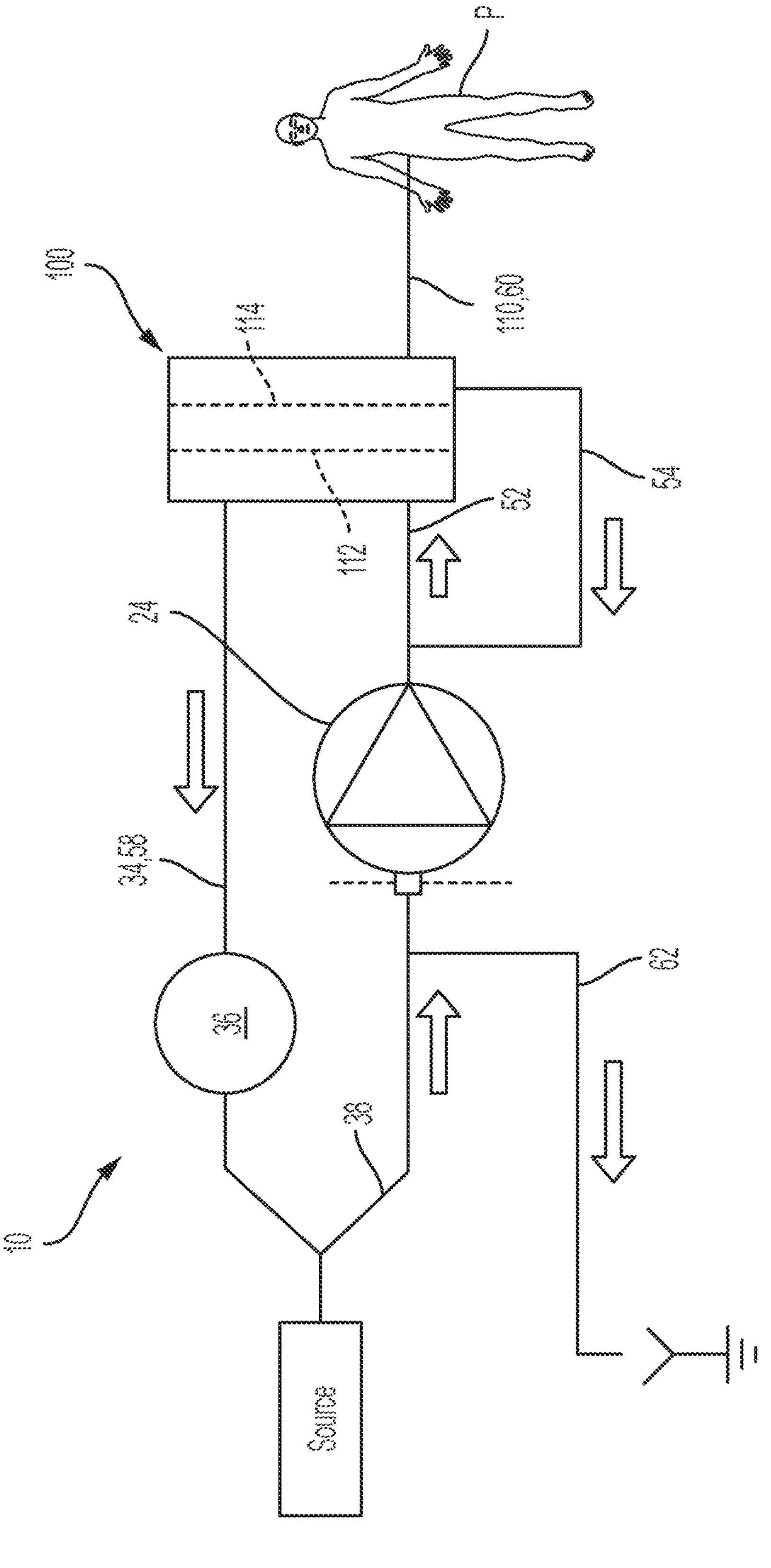
FIG. 4 is a simplified flow schematic illustrating the various flowpaths, including the air return flowpath of the present disclosure.

FIG. 4 illustrates a simplified flow schematic that summarizes the air return flow of system 10 of the present disclosure. Fresh PD fluid pumped by PD fluid pump 24 flows along primary PD fluid line 38 and fresh PD fluid lumen 52 to filter set 100. Air diverting net 112 within filter set 100 diverts air in the fresh PD fluid, while one or more sterilizing grade or bacteria reduction filter membrane(s) 114 further filters the fresh PD fluid, which is delivered to patient P via short, flexible tube 110 (if provided) and patient transfer set 60. Used PD fluid is removed from patient P via PD fluid pump 24 and delivered to drain via patient transfer set 60, short, flexible tube 110 (if provided), filter set 100, used PD fluid lumen 54 and drain line 62. Air and a small amount of PD fluid diverted via air diverting net 112 are delivered back to PD fluid pump 24 via flexible air return line 58, cycler air return line 34 and primary PD fluid line 38. Along the way, air is degassed from the PD fluid via air trap 36.

It should be understood that various changes and modifications to the presently preferred embodiments described herein will be apparent to those skilled in the art. It is therefore intended that any or all of such changes and modifications may be covered by the appended claims. For example, while fresh PD fluid lumen 52 is shown as being located outside of used PD fluid lumen 54 in the concentric embodiment of dual lumen patient line 50, used PD fluid lumen 54 may instead be located outside of fresh PD fluid lumen 52. In another example, the air return features of the present disclosure are used with a single lumen patient line, that is, a dual lumen patient line is not required for the air return features of the present disclosure. In a further example, if dual lumen patient line 50 is disposable, then patient line connector 56 may be eliminated, wherein used PD fluid lumen 54 is instead welded to used PD fluid port 104*b* of lumen-side connector 104, fresh PD fluid lumen 52 is instead welded to fresh PD fluid port 104*a*, and flexible air return line 58 is instead welded to an additional fluid port in fluid communication with cylindrical air/PD fluid return channel 104*d*.

The invention claimed is:

1. A peritoneal dialysis ("PD") system (10) comprising:
- a PD machine (20);
- a patient line (50) extending from the PD machine (20);
- a filter set (100) in fluid communication with the patient line (50), the filter set (100) including an air diverting net (112) configured to divert air from PD fluid flowing through the filter set (100); and
- an air return line (58) positioned to return PD fluid containing air back to the PD machine (20).

2. The PD system (10) according to claim 1, wherein the air diverting net (112) is further configured to allow fresh PD fluid to pass through the air diverting net (112).

3. The PD system (10) according to claim 2, wherein the filter set (100) further includes at least one filter membrane (114) configured to filter the fresh PD fluid that has passed through the air diverting net.

4. The PD system (10) according to claim 3, wherein the filter set (100) is configured such that used PD fluid flows tangentially along the at least one filter membrane (114).

5. The PD system (10) according to claim 3, wherein the at least one filter membrane (114) is a sterilizing grade filter membrane or a bacteria reduction filter membrane.

6. The PD system (10) according to claim 1, wherein the PD machine (20) includes a PD fluid pump (24), and wherein the air return line (58) extends to an air return line (34) of the PD machine (20), the air return line (34) extending to an inlet of the PD fluid pump (24).

7. The PD system (10) according to claim 1, wherein the PD machine (20) includes an airtrap (36), and wherein the air return line (58) extends to an air return line (34) of the PD machine (20), the air return line (34) in fluid communication with the airtrap (36).

8. The PD system (10) according to claim 1, wherein the air return line (58) is coextruded with the patient line (50).

9. The PD system (10) according to claim 1, wherein the patient line (50) includes a patient line connector (56) for connecting to a lumen-side connector (104) of the filter set (100), and wherein the air return line (58) extends from the patient line connector (56) to the PD machine (20).

10. The PD system (10) according to claim 9, wherein the lumen-side connector (104) includes a fresh PD fluid port (104*a*) for receiving fresh PD fluid from the patient line (50), the fresh PD fluid port (104*a*) including at least one opening (104*o*) for allowing air diverted by the air diverting net (112) to be returned to the PD machine (20) via the air return line (58).

11. The PD system (10) according to claim 10, wherein the at least one opening (104*o*) is in fluid communication with a channel (104*d*) formed by the lumen-side connector (104), the channel extending so as to direct air diverted by the air diverting net (112) towards an air return port (56*d*) of the patient line connector (56).

12. The PD system (10) according to claim 1, wherein the patient line (50) connects to a lumen-side connector (104) of the filter set (100), and wherein the air return line (58) extends from the lumen-side connector (104) to the PD machine (20).

13. The PD system (10) according to claim 1, wherein the patient line (50) is a dual lumen patient line including a fresh PD fluid lumen (52) and a used PD fluid lumen (54), and wherein the air return line (58) is a third line extending between the filter set (100) and the PD machine (20).

14. The PD system (10) according to claim 13, which includes a patient line connector (56) for connecting to a lumen-side connector (104) of the filter set (100), and wherein the fresh and used PD fluid lumens (52, 54) are connected to the patient line connector (56).

15. The PD system (10) according to claim 13, wherein the filter set (100) includes a lumen-side connector (104), and wherein the fresh and used PD fluid lumens (52, 54) are connected to the lumen-side connector (104).

16. The PD system (10) according to claim 1, wherein the filter set (100) is configured to connect directly to a patient's transfer set, or wherein the filter set (100) includes a flexible tube (110) configured to connect to the patient's transfer set.

17. A filter set (100) comprising:

a body (106) holding at least one filter membrane (114) positioned and arranged such that fresh PD fluid flows through at least one porous wall of the at least one filter membrane (114) prior to exiting the body (106);

an air diverting net (112) configured to divert air from the fresh PD fluid prior to reaching the at least one filter membrane (114); and a fresh PD fluid port (104*a*) for receiving the fresh PD fluid, the fresh PD fluid port (104*a*) including at least one opening (104*o*) for allowing air diverted by the air diverting net (112) to be returned to a PD machine.

18. The filter set (100) according to claim 17, which includes a channel (104*d*) in fluid communication with the at least one opening (104*o*), the channel (104*d*) extending so as to direct air diverted by the air diverting net (112) for return to the PD machine.

19. The filter set (100) according to claim 17, which includes a connector (104) for connecting to a patient line connector, the air diverting net (112) provided by the connector (104).

20. The filter set (100) according to claim 17, which includes a connector (104) for connecting to a patient line connector, the fresh PD fluid port (104*a*) provided by the connector (104).

21. The filter set (100) according to claim 17, wherein the at least one filter membrane (114) has a tubular, capillary or flat shape.

22. The filter set (100) according to claim 17, which includes (i) a transfer set-side connector (108) configured to connect to a patient's transfer set, or (ii) a flexible line (110) configured to connect to the patient's transfer set.

* * * * *